(12) United States Patent
Chung et al.

(10) Patent No.: US 11,881,120 B2
(45) Date of Patent: Jan. 23, 2024

(54) CLIENT-CUSTOMIZED CARDIOPULMONARY RESUSCITATION SYSTEM

(71) Applicant: INNOSONIAN, INC., Seocho-gu Seoul (KR)

(72) Inventors: Mok Chung, Seocho-gu Seoul (KR); Woong Hur, Seocho-gu Seoul (KR); Olivier Pascal Mercher, Yongsan-gu Seoul (KR); Sung Jin Ryu, Seocho-gu Seoul (KR); Ju Hee Lee, Seongnam-si (KR)

(73) Assignee: INNOSONIAN, INC., Seocho-gu Seoul (KR)

( * ) Notice: Subject to any disclaimer, the term of this patent is extended or adjusted under 35 U.S.C. 154(b) by 0 days.

(21) Appl. No.: 18/013,126

(22) PCT Filed: Jul. 1, 2021

(86) PCT No.: PCT/KR2021/008330
§ 371 (c)(1),
(2) Date: Dec. 27, 2022

(87) PCT Pub. No.: WO2022/010176
PCT Pub. Date: Jan. 13, 2022

(65) Prior Publication Data
US 2023/0245593 A1 Aug. 3, 2023

(30) Foreign Application Priority Data
Jul. 6, 2020 (KR) .................. 10-2020-0082691

(51) Int. Cl.
*G09B 23/28* (2006.01)
*G16H 70/20* (2018.01)

(52) U.S. Cl.
CPC .......... *G09B 23/288* (2013.01); *G16H 70/20* (2018.01)

(58) Field of Classification Search
None
See application file for complete search history.

(56) References Cited

U.S. PATENT DOCUMENTS

2008/0124694 A1\* 5/2008 Miller ...................... G09B 5/00
434/262
2016/0328998 A1\* 11/2016 Pedersen .............. A61B 8/4245

FOREIGN PATENT DOCUMENTS

| JP | 6656151 B2 | 3/2020 |
| KR | 20060073273 A | 6/2006 |

(Continued)

OTHER PUBLICATIONS

International Search Report from corresponding PCT/KR2021/008330 dated Oct. 18, 2021.

(Continued)

*Primary Examiner* — James B Hull
(74) *Attorney, Agent, or Firm* — Sandberg Phoenix & von Gontard, PC

(57) ABSTRACT

A client-customized cardiopulmonary resuscitation system, according to one embodiment, may comprise: a training device for practicing cardiopulmonary resuscitation; a terminal which can communicate with the training device and acquires information on a user's cardiopulmonary resuscitation operation performed in the training device; and a server which can communicate with the terminal and provides a manager page which enables a client to directly edit the configuration of a screen displayed on the terminal.

11 Claims, 9 Drawing Sheets

(56) References Cited

FOREIGN PATENT DOCUMENTS

| | | |
|---|---|---|
| KR | 20100078493 A | 7/2010 |
| KR | 20120102178 A | 9/2012 |
| KR | 20160092805 A | 8/2016 |
| KR | 20190018102 A | 2/2019 |
| KR | 102099460 B1 | 4/2020 |

OTHER PUBLICATIONS

Office Action from related Korean App. No. 10-2021-0143467 dated Apr. 28, 2022.
Notice of Allowance from related Korean App. No. 10-2021-0143467 dated Oct. 24, 2022.

* cited by examiner

CLIENT-CUSTOMIZED CARDIOPULMONARY RESUSCITATION SYSTEM

CROSS-REFERENCE TO RELATED APPLICATIONS

This application is the US National Stage under 35 USC § 371 of International Application No. PCT/KR2021/008330 filed Jul. 1, 2021 which claims priority to KR App. No. 10-2020-0082691 filed Jul. 6, 2020, both of which are incorporated herein by reference.

TECHNICAL FIELD

The following description relates to a client-customized cardiopulmonary resuscitation (CPR) system.

BACKGROUND ART

Cardiopulmonary resuscitation (CPR) is an emergency treatment that restores and revives a cardiopulmonary function when the cardiopulmonary function is severely degraded or suspended. CPR circulates blood in a state of heart failure to provide a decisive help in delaying damage to the brain and recovering from heart failure. CPR may be performed in different ways depending on whether a target is an adult, a child, or an infant. Therefore, it may be important to understand and learn in advance how to do CPR for each target. In general, such CPR training may be provided as two-dimensional training using displays or booklets, and thus it may not be effectively delivered to trainees. Therefore, to increase the effects of the training, there is a need for a training device configured to enable a user to directly practice CPR in a similar situation to an actual situation. In addition, there is a need for a system in which the training device and a terminal interwork together and the terminal is used to monitor a practice situation and receive feedback on a result of a practice operation. Further, a protocol for performing CPR may vary from country to country or hospital to hospital, and thus there is a need for a system that enables each client to directly design and edit a CPR training program even when the same training device is used.

The above description is information the inventor(s) acquired during the course of conceiving the present disclosure, or already possessed at the time, and is not necessarily art publicly known before the present application was filed.

DISCLOSURE

Technical Goals

An objective of an embodiment is to provide a cardiopulmonary resuscitation (CPR) system in which a training device, a terminal, and a server interwork with each other.

An objective of an embodiment is to provide a CPR system with which a client is able to directly configure a screen to be displayed on a terminal.

An objective of an embodiment is to provide a CPR system configured to provide statistics on CPR practices.

Technical Solutions

According to an embodiment, a client-customized cardiopulmonary resuscitation (CPR) system includes a training device for practicing CPR, a terminal configured to communicate with the training device and obtain information on a CPR operation performed by a user on the training device, and a server configured to communicate with the terminal and provide a manager page that allows a client to directly edit a configuration of a screen to be displayed on the terminal.

The server may assign a client identification (ID) to each client, and the client may access the manager page with an assigned corresponding client ID to edit the screen to be displayed on the terminal, and the edited screen may be displayed on the terminal logged in with the client ID.

The screen displayed on the terminal may include at least one of a title, an image, a video, or a training program.

The client may configure, through the manager page, at least one of a training title, a training type, a feedback type, an auto-stop, a chest compression-to-ventilation ratio, rescue ventilation, certificate issuance, a display icon, a display number, or a display position of the training program.

When CPR training for the user ends, the terminal may transmit the information on the CPR operation of the user to the server, and the server may analyze the received information on the CPR operation of the user, calculate an assessment result of assessing the CPR operation of the user, and transmit the calculated assessment result to the terminal.

The terminal may display the assessment result of the CPR operation of the user received from the server and issue a certificate according to the assessment result of the CPR operation of the user.

The client may edit an item indicated in the certificate through the manager page.

The server may include a main instance and at least one auxiliary instance.

The terminal may communicate with the main instance, and communicate with the auxiliary instance when the main instance goes down.

The server may include a plurality of instances, and the terminal may communicate with an instance having a highest reaction speed among the plurality of instances.

The client may create and manage a user account of each user on the manager page. When the user logs into the terminal with a corresponding user account and uses the training device, CPR training information of the user may be transmitted to the server.

The server may record CPR training information for each user and provide CPR training information statistics for each user.

The client may edit an item indicated in the statistics on the manager page.

The server may provide training device usage statistics for each training device.

The information on the CPR operation of the user may include at least one of a chest compression depth, a chest compression speed, a chest compression position, or a ventilation volume.

Effects

A cardiopulmonary resuscitation (CPR) system according to an embodiment may record and analyze information on practices, with a training device, a terminal, and a server interworking with each other therein.

A CPR system according to an embodiment may enable a client to edit a screen to be displayed on a terminal, items of a certificate, items of statistics, or the like.

A CPR system according to an embodiment may improve communication stability using a plurality of instances.

The effects of the CPR system according to embodiments are not limited to the foregoing effects, and other effects that are not described above may be clearly understood from the following description by those having ordinary skill in the art.

BRIEF DESCRIPTION OF DRAWINGS

FIG. 4 illustrates a screen for editing in detail a training program on a manager page of a server of a CPR system according to an embodiment.

FIG. 5 illustrates a screen for managing user accounts on a manager page of a server of a CPR system according to an embodiment.

BEST MODE FOR CARRYING OUT INVENTION

Figure 1:
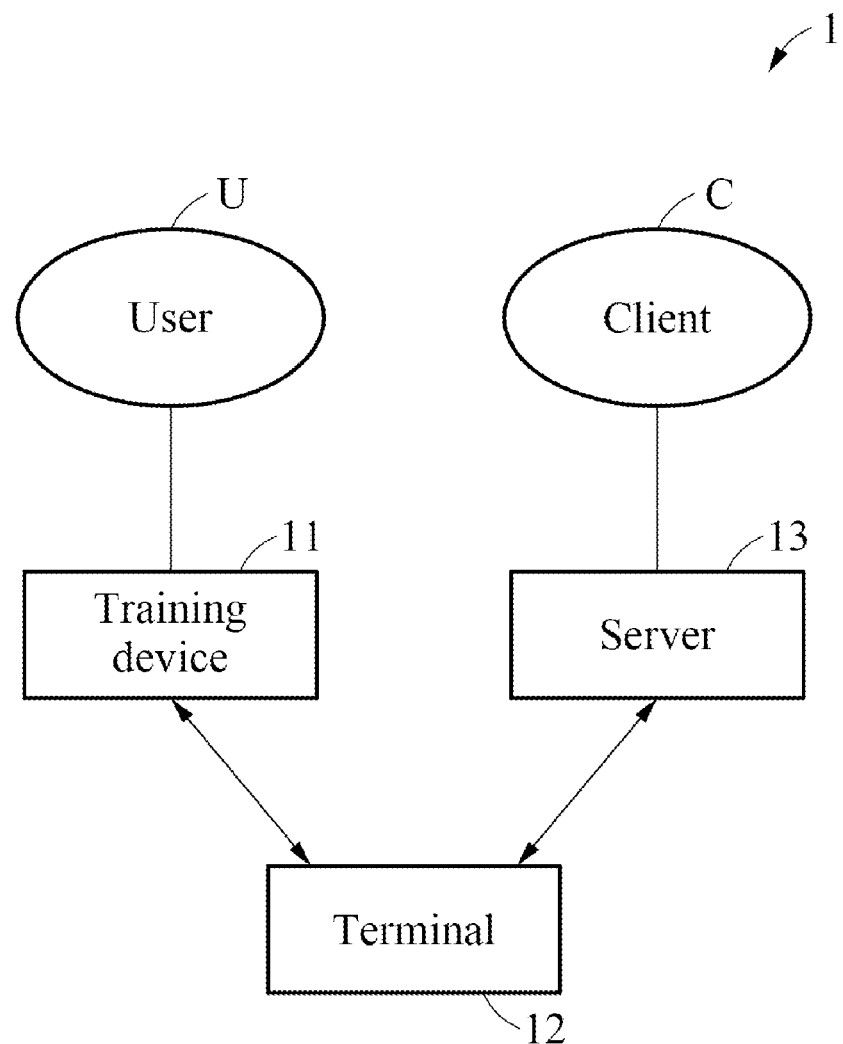
FIG. 1 is a block diagram illustrating a cardiopulmonary resuscitation (CPR) system according to an embodiment.

Hereinafter, example embodiments will be described in detail with reference to the accompanying drawings. However, various modifications may be made to the example embodiments, and the scope of matters claimed herein are not limited or restricted by these example embodiments. The example embodiments should be understood to include all changes, equivalents, and replacements within the idea and the technical scope of the present disclosure.

The terms used herein are for the purpose of describing particular example embodiments only and are not to be limiting of the example embodiments. The singular forms "a," "an," and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments pertain. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, when describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

In addition, in the description of the components, terms such as first, second, A, B, (a), (b) or the like may be used herein when describing components of the example embodiments. These terms are used only for the purpose of discriminating one element from another element, and the nature, the sequences, or the orders of the elements are not limited by the terms. When one element is described as being "connected," "coupled," or "attached" to another element, it should be understood that one element may be connected or attached directly to another element, and an intervening element may also be "connected," "coupled," or "attached" to the elements.

The same name may be used to describe an element included in one example embodiment and an element having a common function as the foregoing element in another example embodiment. Unless otherwise defined, the description of the example embodiments may be applicable to the following example embodiments and a repeated description related thereto will be omitted for conciseness.

FIG. 1 is a block diagram illustrating a cardiopulmonary resuscitation (CPR) system according to an embodiment.

Referring to FIG. 1, a CPR system 1 according to an embodiment may record and analyze a CPR operation performed by a user U and provide an analysis result obtained therefrom to the user U, thereby providing effective CPR training to the user U. The user U may refer to herein an individual person who practices CPR themselves using a training device 11.

The CPR system 1 may be customized and editable for a client C to provide functions and items desired by the client C. The client C may refer to herein a customer who desires to use the CPR system 1. The client C may include, for example, a hospital, a fire station, a government office, an enterprise, a school, or the like.

According to an embodiment, the CPR system 1 may include the training device 11, a terminal 12, and a server 13.

The training device 11 may be a device with which the user U may practice CPR. The training device 11 may have a similar exterior to a human body to provide the user U with a similar feeling to that they have in a real situation. For example, the training device 11 may have an external shape according to a standard human body shape. The training device 11 may be classified into one for adults, one for children, and one for infants, and may include a mannequin having an appearance of an adult, a child, and an infant, respectively. The training device 11 may be configured such that a series of operations for CPR, for example, chest compression, ensuring free airway, artificial ventilation, and the like, is performed The terminal 12 may be a separate device capable of communicating with the training device 11. The terminal 12 may include a display and/or a speaker to visually and/or audibly provide information to the user U. The terminal 12 may include, for example, a smartphone, a tablet, a personal computer (PC), a personal digital assistant (PDA), a smartwatch, or the like, and may use applications or websites. The terminal 12 may communicate with a plurality of training devices 11.

The server 13 may communicate with the terminal 12. For example, the server 13 may communicate with a plurality of terminals 12 individually. The server 13 may perform an operation of analyzing information provided by the terminal 12. In addition, the server 13 may provide a manager page 130 to the client C. The manager page 130 will be described later.

The server 13 may assign a unique client identification (ID) to each client C. The client C may access the manager page 130 with an assigned corresponding client ID. The client C may edit a screen to be displayed on the terminal 12 on the manager page 130. The edited screen may be displayed on the terminal 12 logged in with the client ID. That is, the client C may directly edit the screen to be displayed on the terminal 12 on the manager page 130 of the server 13 using the unique client ID, and log in with the client ID in the terminal 12 to display the screen directly edited by the client C. That is, such a configuration may implement a screen configuration of the terminal 12 unique to each client C.

The screen displayed on the terminal 12 may include at least one of a title, an image, a video, or a training program 21.

The client C may edit the title to be displayed on the screen of the terminal 12 through the manager page 130. In addition, the client C may select an image and/or a video to be displayed on the screen of the terminal 12 through the manager page 130. For example, the client C may allow an image or video introducing the corresponding client C or an image or video guiding CPR training to be displayed on the terminal 12.

Figure 2:
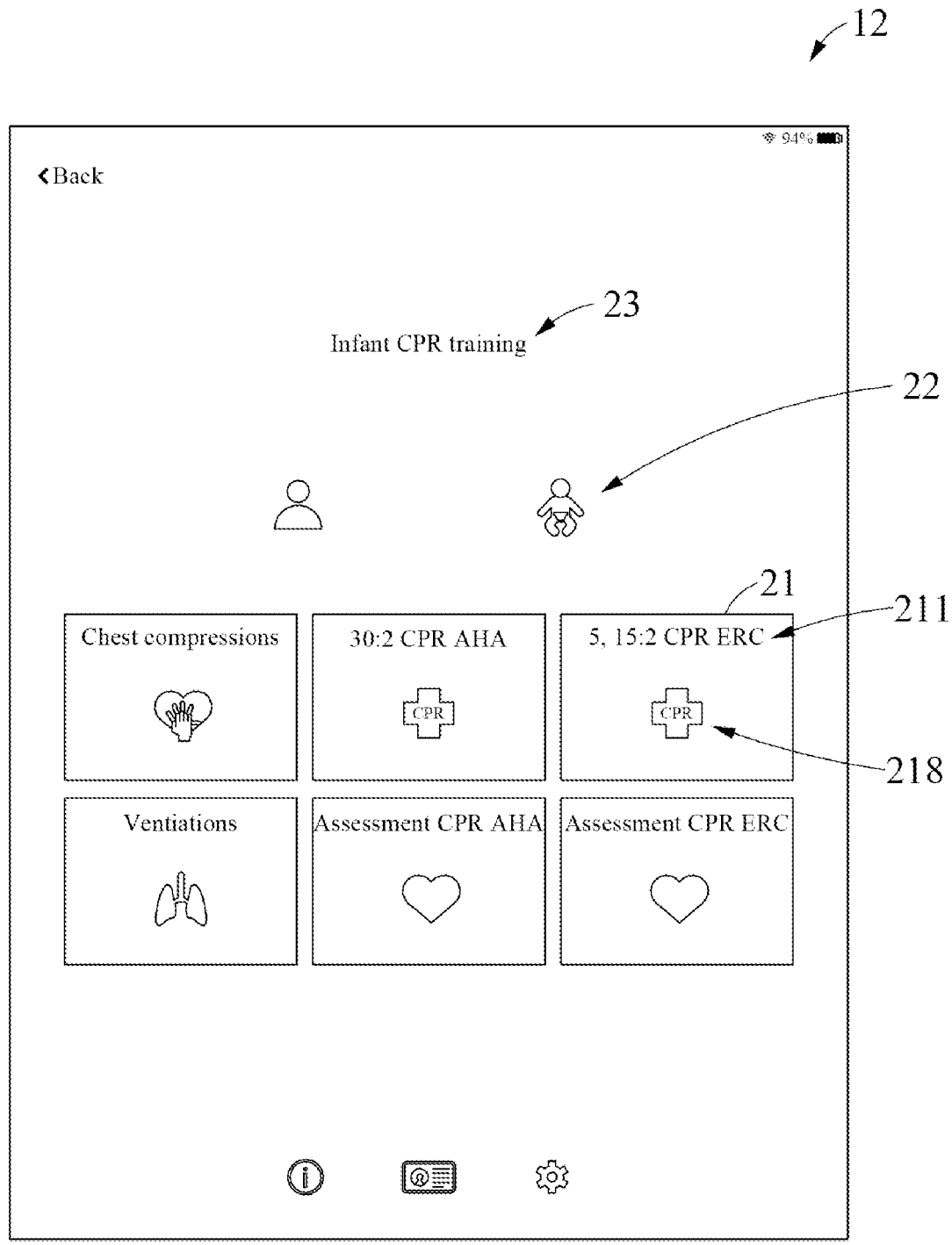
FIG. 2 illustrates a screen displayed on a terminal of a CPR system according to an embodiment.
Figure 3:
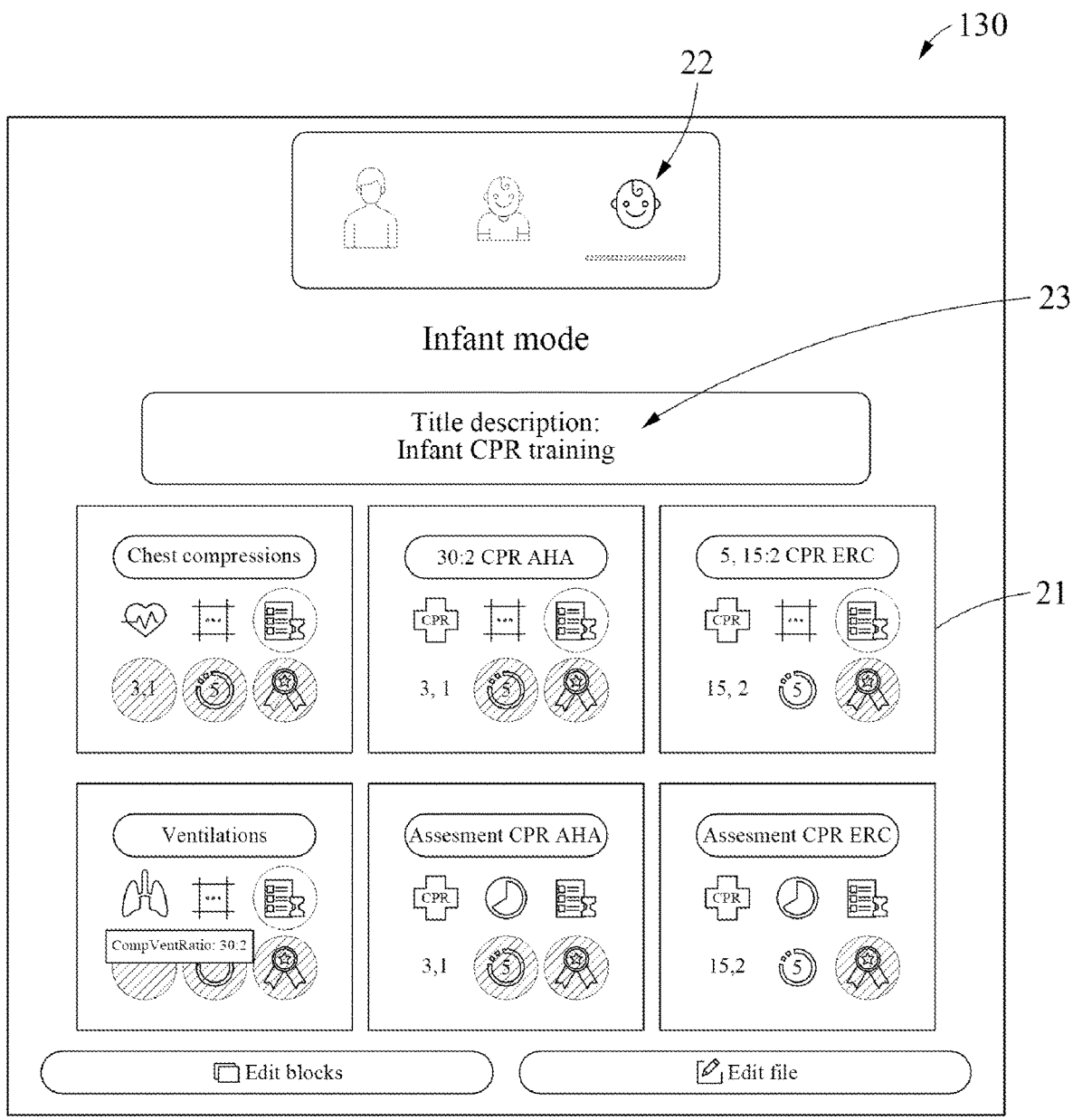
FIG. 3 illustrates a screen for editing a training program on a manager page of a server of a CPR system according to an embodiment.
Figure 4:
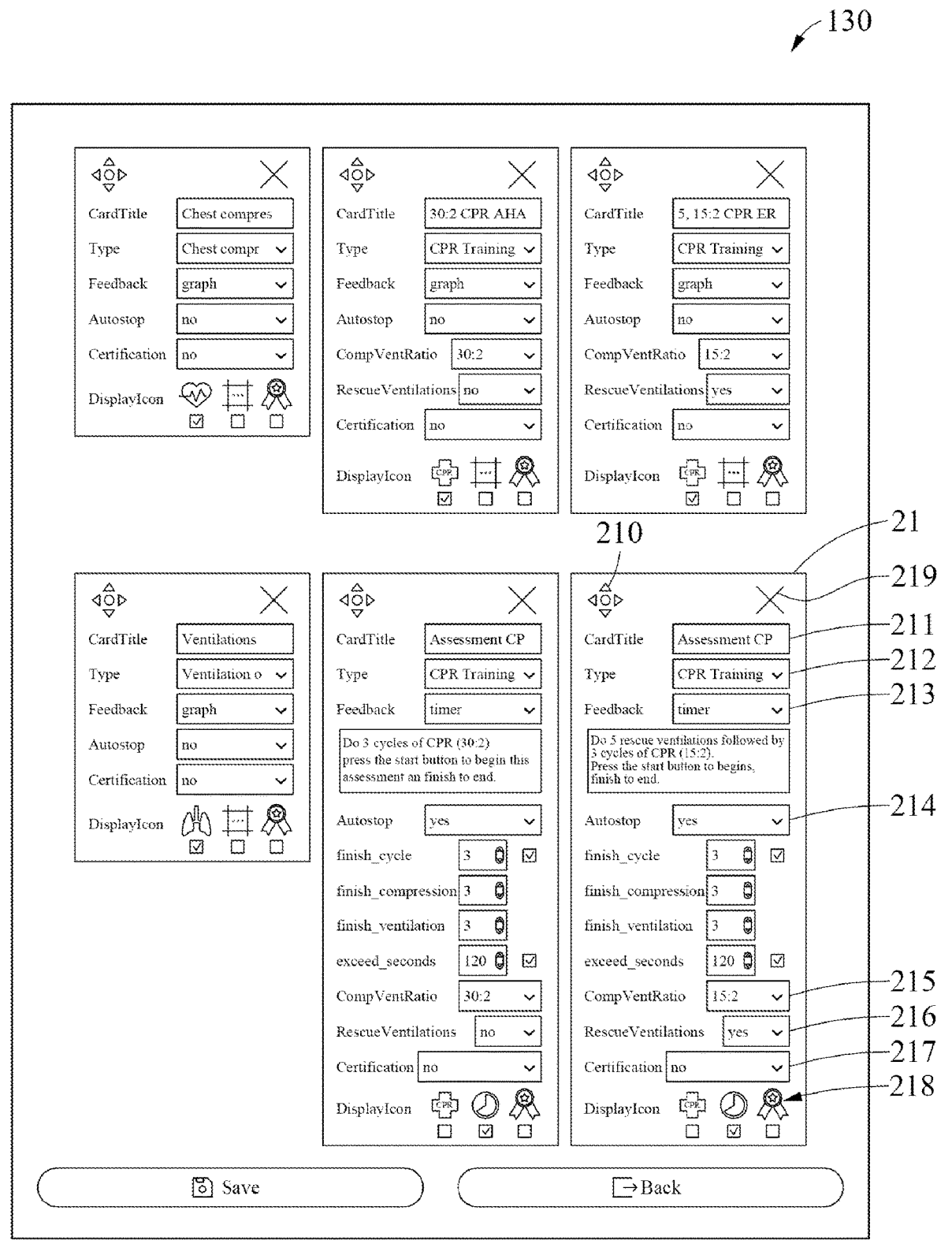

FIG. 2 illustrates a screen displayed on a terminal of a CPR system according to an embodiment. FIG. 3 illustrates a screen for editing a training program on a manager page of a server of a CPR system according to an embodiment. FIG. 4 illustrates a screen for editing in detail a training program on a manager page of a server of a CPR system according to an embodiment.

Referring to FIGS. 2 to 4, a client C may edit the training program 21 to be displayed on the terminal 12 through the manager page 130. The training program 21 may be a CPR training program configured in advance by the client C. For example, the client C may set or configure a training program 21 for each type 22 of training device 11. The set training program 21 for each type 22 of training device 11 may be displayed on a screen of the terminal 12 to correspond to each type 22 of a training device connected to the terminal 12. For example, when a training device 11 for adults is connected to the terminal 12, a training program 21 for adults may be displayed on the screen of the terminal 12, and when a training device 11 for infants is connected to the terminal 12, a training program 21 for infants may be displayed. The client C may set a title 23 for each type 22 of training device 11. The set title 23 for each type 22 of training device 11 may be displayed on the screen of the terminal 12 to correspond to a type 22 of a training device connected to the terminal 12.

As shown in FIG. 4, a client C may set detailed contents of each training program 21 through the manager page 130. For example, the client C may set at least one of a training title 211, a training type 212, a feedback type 213, an auto-stop 214, a chest compression-to-ventilation ratio 215, a rescue ventilation 216, a certificate issuance 217, a display icon 218, a display number 219, or a display position 210 of each training program 21.

The client C may set the training title 211 and the display icon 218 of each training program 21. The display icon 218 may include, for example, icons of various items such as CPR, chest compression, artificial ventilation, and certificates. As shown in FIG. 2, the training title 211 and the display icon 218 may be displayed together on the screen of the terminal 12. A user U may thereby identify the contents of the training program 21 through the training title 211 and the display icon 218 displayed on the terminal 12.

The client C may set the training type 212 of each training program 21. The training type 212 may include CPR training, chest compression training, and artificial ventilation training. The client C may set the feedback type 213 of each training program 21. The feedback type 213 may include a graph type and a timer type. The client C may set the auto-stop 214 of each training program 21. The auto-stop 214 may be a function of automatically ending training after a predetermined operation or a predetermined time. The client C may set whether to apply the auto-stop 214 of each training program 21, and when applying the auto-stop 214, the client C may set at least one of an end cycle, an end compression number, an end ventilation number, or an end time. The client C may set the chest compression-to-ventilation ratio 215 of each training program 21. The chest compression-to-ventilation ratio 215 may include 30:2, 15:2, and 3:1. Accordingly, the client C may configure a client-customized training program by setting the chest compression-to-ventilation ratio 215 corresponding to a corresponding client CPR protocol. The client C may set whether to perform the rescue ventilation 216 of each training program 21. The client C may set whether to issue the certificates 217 for each training program 21. A certificate described herein may be a certificate to be issued when the user U performs a corresponding training program 21 according to standards.

The client C may set the display number 219 and the display position 210 of each training program 21. For example, the client C may rearrange a position of a training program 21 by dragging a block, and may set a desired number of training programs 21 by adjusting the display number 219.

By this configuration, each client C may be able to configure a screen to be displayed on the terminal 12 autonomously, and each client C may thus configure an individual training program 21. Therefore, a plurality of clients C may configure their own training programs 21 using the same CPR system 1, and thus the degree of freedom of each client C may increase. In addition, even for clients C having different CPR protocols, they may be able to configure their training programs 21 individually, and it may thus be possible to improve the versatility of the CPR system 1 and convenience in the maintenance of the CPR system 1.

Figure 5:
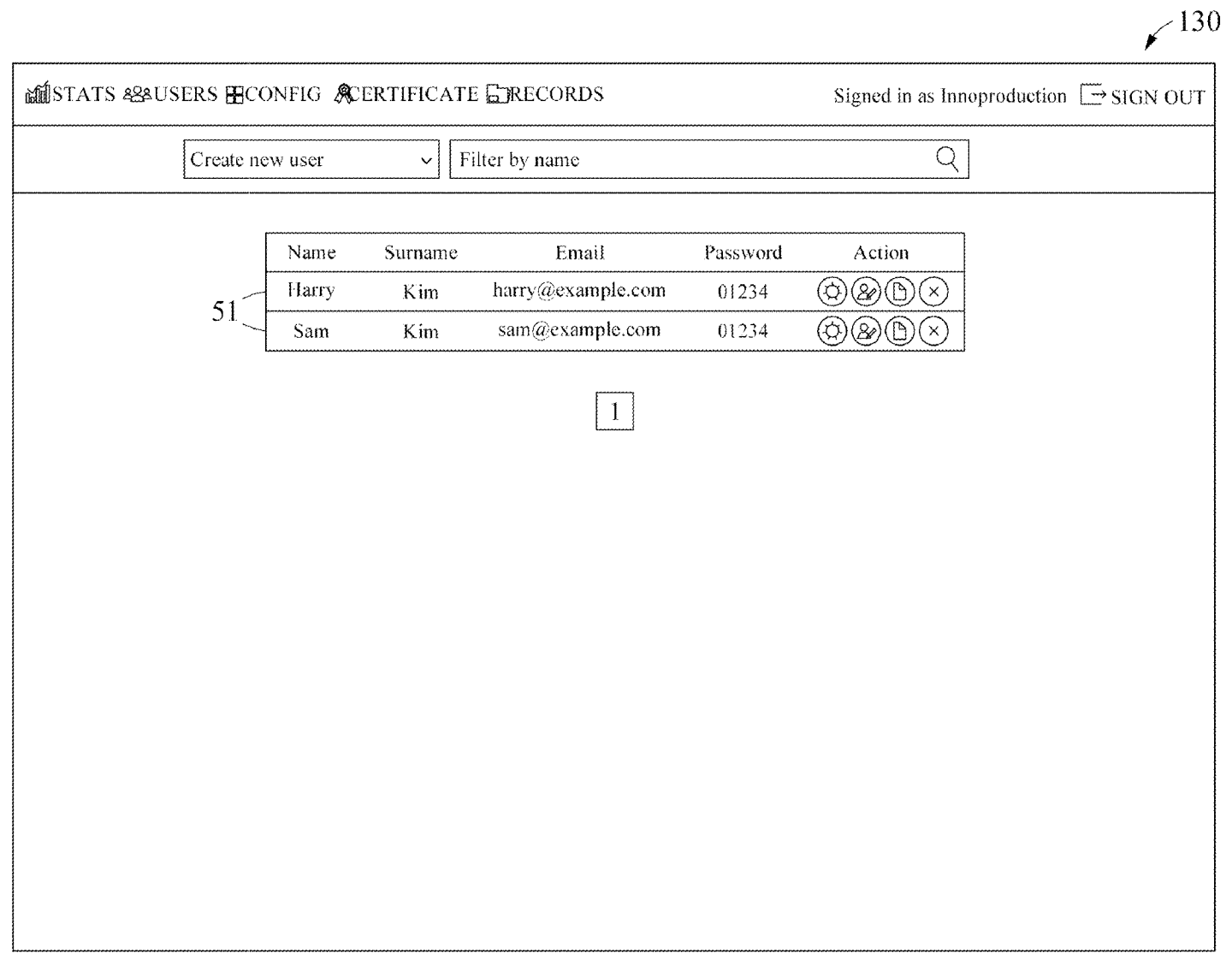

FIG. 5 illustrates a screen for managing user accounts on a manager page of a server of a CPR system according to an embodiment.

Referring to FIG. 5, a client C may manage a user account 51 of each user U on the manager page 130. For example, the client C may create and edit the user account 51. The user account 51 may be a unique account created for each user U. The user account 51 may include information about a name, an email, a password, and the like of a user U. The user U may log in to the terminal 12 with the user account 51. For example, when the client C logs in to the terminal 12 with a client ID, the user U may log in to the terminal 12 with the user account 51. When the user U logs in to the terminal 12 with the user account 51 and performs training using the training device 11, CPR training information of the user U may be transmitted to the server 13. The server 13 may then record received CPR training information for each user U. The server 13 may also provide statistics on the CPR training information for each user U. In addition, the client C may edit items indicated in the statistics on the CPR training information for each user U on the manager page 130. For example, the statistics on the CPR training information for each user U may include items related to user information, a training device type, a chest compression depth, a chest compression speed, a chest compression position, a ventilation volume, the number of training sessions, a training period, a training time, an assessment result, or the like. The statistics may be provided as graphs or charts.

When the CPR training for the user U progresses, the training device 11 may transmit CPR operation information of the user U to the terminal 12. The CPR operation information of the user U may include, for example, at least one of a chest compression depth, a chest compression speed, a chest compression position, or a ventilation volume. During the CPR training, the terminal 12 may obtain and store the CPR operation information of the user U transmitted from the training device 11. In addition, the terminal 12 may provide the CPR operation information on a CPR operation performed by the user U on the training device 11 to the user U in real time. The user U may receive feedback on the CPR operation by monitoring their own CPR operation information through the terminal 12 in real time.

When the CPR training for the user U ends, the terminal 12 may transmit the stored CPR operation information of the user U to the server 13. That is, the terminal 12 may communicate with the training device 11 while the CPR training is being performed, and may communicate with the server 13 when the CPR training ends. This configuration may reduce communication interface and may thus improve system stability.

The server 13 may analyze the received CPR operation information of the user U. The server 13 may indicate, as numbers, the CPR operation information and calculate an assessment result of assessing the CPR operation of the user U. The server 13 may transmit the calculated assessment result to the terminal 12, and the terminal 12 may display the received assessment result on the screen. The user U may receive feedback on the CPR operation through the assessment result displayed on the terminal 12. When such an operation of analyzing the CPR operation information and calculating the assessment result is performed as described above in the server 13 instead of the terminal 12, a system manager may update an assessment algorithm onto the server 13 and may thereby collectively manage it. That is, when updating the assessment algorithm, updating the server 13, instead of individual terminals 12, may thereby enable collective updating and reduce a burden on system management and increase convenience in management.

Figure 6:
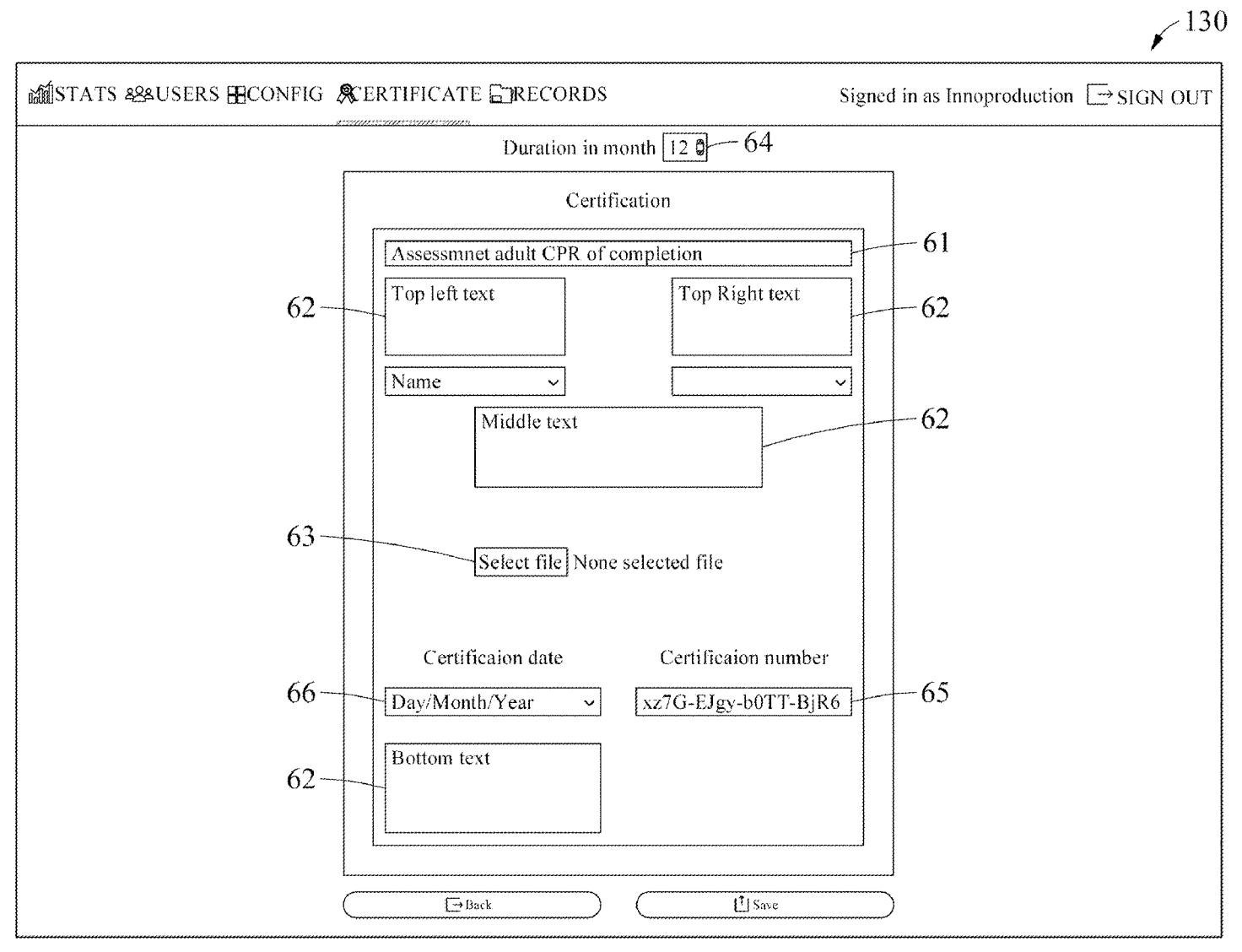

In addition, the terminal 12 may issue a certificate based on the assessment result. For example, when the assessment result satisfies a predetermined standard, the terminal 12 may issue the certificate indicating that the user U has completed a training program. The certificate may be transmitted to an email stored in the user account 51. FIG. 6 illustrates a screen for editing a certificate on a manager page of a server of a CPR system according to an embodiment. Referring to FIG. 6, a client C may edit items indicated in a certificate on the manager page 130. For example, the client C may edit a certificate title 61, a certificate content 62, an attached image 63, a certification period 64, a certificate number 65, a certification date 66, or the like.

Figure 7:
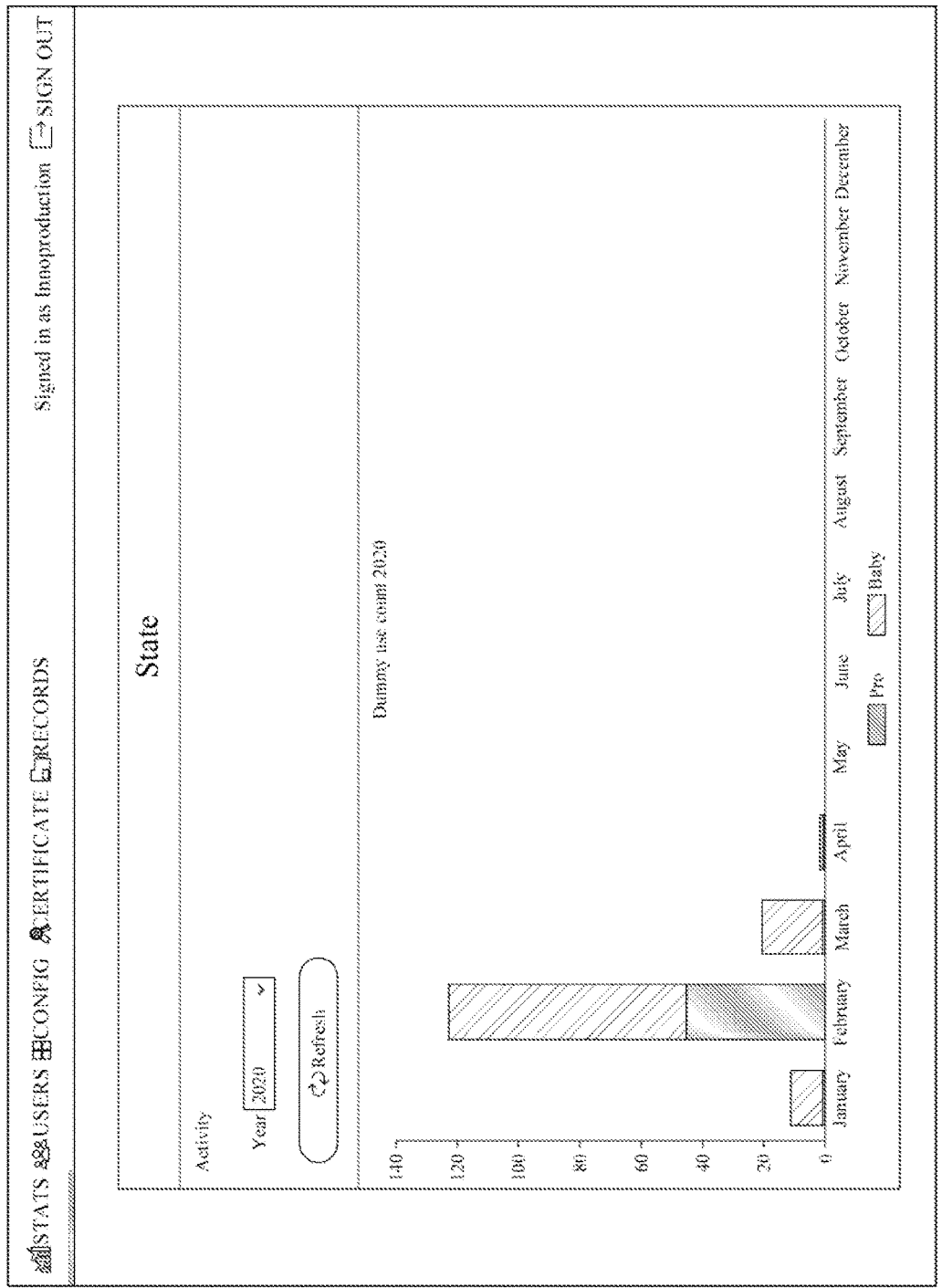
FIG. 7 illustrates a screen showing training device usage statistics for each training device provided on a manager page of a server of a CPR system according to an embodiment.

FIG. 7 illustrates a screen showing training device usage statistics for each training device provided on a manager page of a server of a CPR system according to an embodiment.

Referring to FIG. 7, the server 13 may provide training device usage statistics for each training device 11 on the manager page 130. The server 13 may store training device usage records of each training device 11 and process the statistics. For example, the server 13 may display the number of times of use of each type of training device 11 by month or year in a graph. A client C may then check the usage statistics for each training device 11 and determine the demand for each type of training device 11.

Figure 8:
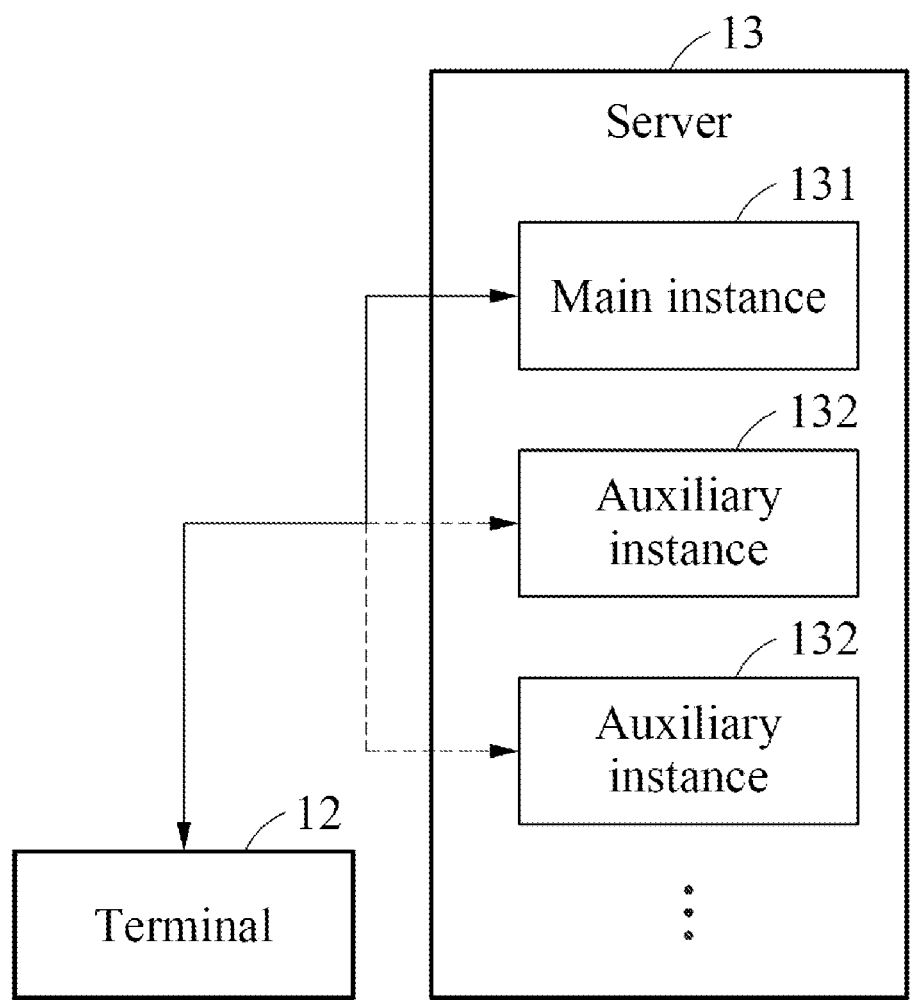
FIGS. 8 and 9 are block diagrams illustrating a plurality of instances of a server of a CPR system according to an embodiment.
Figure 9:
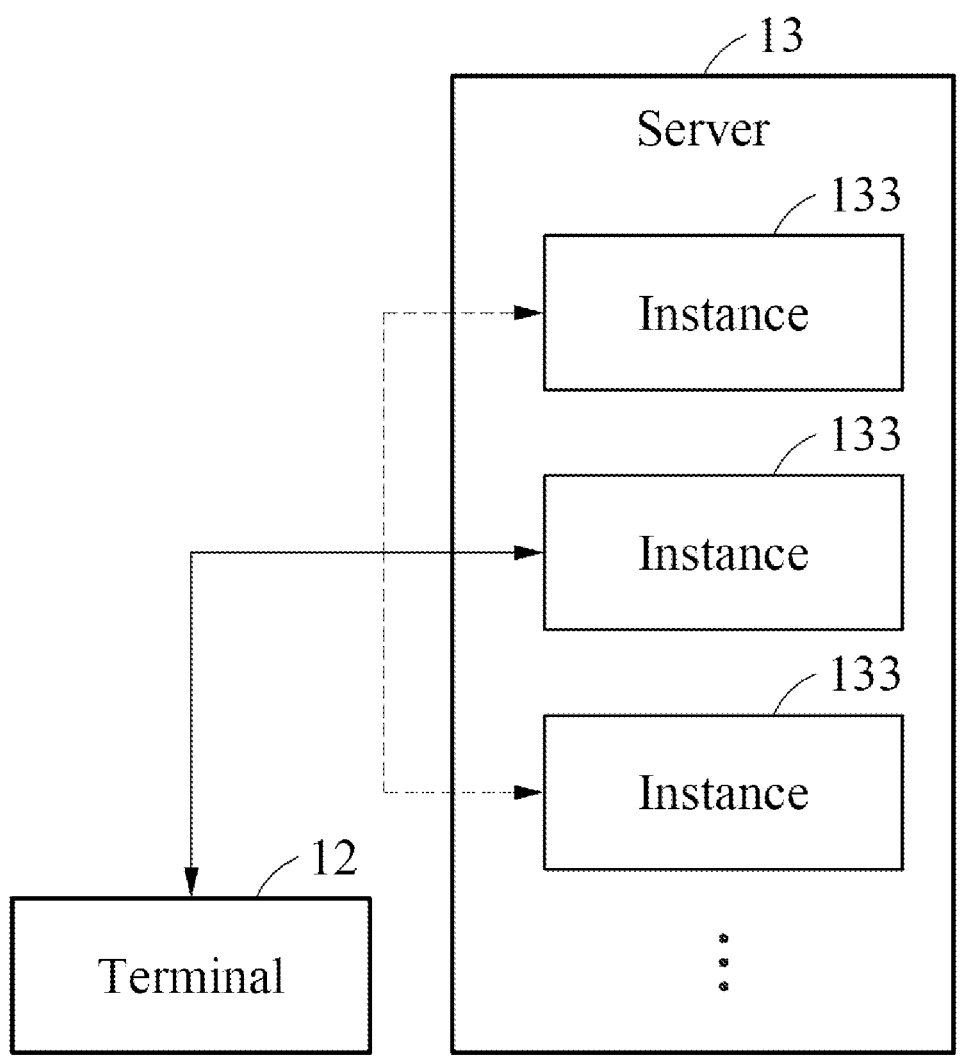

FIGS. 8 and 9 are block diagrams illustrating a plurality of instances of a server of a CPR system according to an embodiment.

Referring to FIGS. 8 and 9, the server 13 may include a plurality of instances when communicating with the terminal 12. Referring to FIG. 8, the server 13 may include a main instance 131 and at least one auxiliary instance 132. The terminal 12 may be configured to communicate with the main instance 131 by default. However, when the main instance 131 goes down, the terminal 12 may communicate with the auxiliary instance 132. This configuration may separate the main and the auxiliary and may thereby improve server stability. Alternatively, referring to FIG. 9, the server 13 may include a plurality of instances 133. The terminal 12 may communicate with an instance having a highest reaction speed among the plurality of instances 133. This configuration may prevent traffic concentration and may thereby improve server stability.

A number of example embodiments have been described above. Nevertheless, it should be understood that various technical changes and modifications may be made to these embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

The invention claimed is:

1. A method of using a client-customized cardiopulmonary resuscitation (CPR) system in which a client is a CPR trainer and a user is a CPR trainee, the client-customized CPR system comprising:
 a training device for practicing CPR;
 a terminal configured to communicate with the training device and to obtain information on a CPR operation performed by the user on the training device; and
 a server configured to communicate with the terminal and provide a manager page that allows the client to directly edit a configuration of a screen including a training program to be displayed on the terminal,
 wherein the configuration of the screen to be displayed on the terminal further comprises at least one of a title, an image, or a video, and
 wherein the server is configured to assign a client identification (ID) to each client,
 the method comprising:
 the client accessing the manager page with an assigned client ID to edit the configuration of the screen to be displayed on the terminal and design the training program to be displayed on the terminal, and as the edited configuration of the screen comprising the designed training program is displayed on the terminal logged in with the client ID, the client has a unique screen configuration displayed on the terminal,
 the client creating and managing a user account for each user on the manager page,
 wherein, when the user logs in with the user account to the terminal logged in using the client ID to execute CPR training and performs the CPR training with the training program designed by the client, CPR training information of the user is transmitted to the server.

2. The method of claim 1, wherein the client further edits the configuration, through the manager page, of at least one of a feedback type, an auto-stop, a chest compression-to-ventilation ratio, rescue ventilation, certificate issuance, a display icon, a display number, or a display position of the training program.

3. The method of claim 1, wherein, when the CPR training for the user ends, the terminal transmits the information on the CPR operation of the user to the server, and the server analyzes the received information on the CPR operation of the user, calculates an assessment result of assessing the CPR operation of the user, and transmits the calculated assessment result to the terminal.

4. The method of claim 3, wherein the terminal displays the assessment result of the CPR operation of the user received from the server and issues a certificate according to the assessment result of the CPR operation of the user.

5. The method of claim 4, wherein the client edits an item indicated in the certificate through the manager page.

6. The client customized CPR system method of claim 3, wherein the server comprises a main instance and at least one auxiliary instance,
   wherein the terminal communicates with the main instance, and communicates with the auxiliary instance when the main instance goes down.

7. The method of claim 3, wherein the server comprises a plurality of instances,
   wherein the terminal communicates with an instance having a highest reaction speed among the plurality of instances.

8. The method of claim 1, wherein the server records CPR training information for each user, and provides CPR training information statistics for each user.

9. The method of claim 8, wherein the client edits an item indicated in the statistics on the manager page.

10. The method of claim 1, wherein the server provides training device usage statistics for each training device.

11. The method of claim 1, wherein the information on the CPR operation of the user comprises at least one of a chest compression depth, a chest compression speed, a chest compression position, or a ventilation volume.

\* \* \* \* \*